United States Patent
Gao et al.

(10) Patent No.: US 12,138,341 B1
(45) Date of Patent: Nov. 12, 2024

(54) DISSOLVING MICRONEEDLE CONTAINING CANNABIDIOL SUSPENSION AND PREPARATION METHOD THEREOF

(71) Applicants: Technical Institute of Physics and Chemistry, CAS, Beijing (CN); Beijing CAS Microneedle Technology Ltd., Beijing (CN)

(72) Inventors: Yunhua Gao, Beijing (CN); Aguo Cheng, Beijing (CN); Han Liu, Beijing (CN); Suohui Zhang, Beijing (CN)

(73) Assignees: Technical Institute of Physics and Chemistry, CAS, Beijing (CN); Beijing CAS Microneedle Technology Ltd., Beijing (CN)

( * ) Notice: Subject to any disclaimer, the term of this patent is extended or adjusted under 35 U.S.C. 154(b) by 0 days.

(21) Appl. No.: 18/629,986

(22) Filed: Apr. 9, 2024

(30) Foreign Application Priority Data

Jul. 26, 2023 (CN) .......................... 202310918980.2

(51) Int. Cl.
| | |
|---|---|
| A61K 9/00 | (2006.01) |
| A61K 31/00 | (2006.01) |
| A61K 47/06 | (2006.01) |
| A61K 47/10 | (2017.01) |
| A61K 47/20 | (2006.01) |
| A61K 47/26 | (2006.01) |
| A61K 47/32 | (2006.01) |
| A61K 47/36 | (2006.01) |
| A61K 47/38 | (2006.01) |
| A61M 37/00 | (2006.01) |

(52) U.S. Cl.
CPC .......... *A61K 9/0021* (2013.01); *A61K 31/658* (2023.05); *A61K 47/06* (2013.01); *A61K 47/10* (2013.01); *A61K 47/20* (2013.01); *A61K 47/26* (2013.01); *A61K 47/32* (2013.01); *A61K 47/36* (2013.01); *A61K 47/38* (2013.01); *A61M 2037/0023* (2013.01); *A61M 2037/0053* (2013.01)

(58) Field of Classification Search
CPC .... A61K 9/0021; A61K 31/658; A61K 47/06; A61K 47/10; A61K 47/20; A61K 47/26; A61K 47/32; A61K 47/36; A61K 47/38; A61M 2037/0023; A61M 2037/0053
See application file for complete search history.

(56) References Cited

U.S. PATENT DOCUMENTS

2022/0047541 A1* 2/2022 Plakogiannis ......... A61K 47/22

FOREIGN PATENT DOCUMENTS

| CN | 114588131 A | 6/2022 |
| CN | 114652678 A | 6/2022 |
| CN | 115120565 A | 9/2022 |

OTHER PUBLICATIONS

Lan et al. (CN114832226A Machine English translation) (Year: 2022).*
CNIPA, Notification of First Office Action for CN202310918980.2, Aug. 28, 2023.
Institute of Physical and Chemical Technology, Chinese Academy of Sciences and Zhongke Micro Needle (Beijing) Technology Co., Ltd (Applicants), Reply to Notification of First Office Action for CN202310918980.2, w/ (allowed) replacement claims, Sep. 13, 2023.
CNIPA, Notification to grant patent right for invention in CN202310918980.2, Sep. 26, 2023.

* cited by examiner

*Primary Examiner* — Robert A Wax
*Assistant Examiner* — Quanglong N Truong
(74) *Attorney, Agent, or Firm* — Hemisphere Law, PLLC; Zhigang Ma

(57) ABSTRACT

A nanonization method for cannabidiol (CBD) includes following steps: the CBD is dissolved in a good solvent to obtain a CBD-good solvent solution, the CBD-good solvent solution is added to aqueous solution of a stabilizer to obtain mixed solution, the mixed solution is ultrasonicated followed by removing the good solvent by rotary evaporation from the mixed solution to obtain a nanosized CBD suspension. The stabilizer includes one or more selected from the group consisting of poloxamer, tween, polyoxyethylene alkyl ether, polyvinyl pyrrolidone, hydroxypropyl methyl cellulose and carboxymethyl chitosan. Particle size of the CBD is reduced in the nanonization method for the CBD through the nanonization of insoluble drugs to obtain the nanosized CBD suspension. In the nanosized CBD suspension, nanosized CBD has high solid content. The nanonization method for the CBD achieves solubilization of the CBD.

5 Claims, 4 Drawing Sheets

DISSOLVING MICRONEEDLE CONTAINING CANNABIDIOL SUSPENSION AND PREPARATION METHOD THEREOF

TECHNICAL FIELD

The disclosure relates to the technical field of nanonization of cannabidiol (CBD), and more particularly to a nanonization method for CBD, a nanosized CBD suspension prepared by the nanonization method, and its application.

BACKGROUND

CBD, one of the most abundant cannabinoids in industrial hemp, is not psychoactive and is basically free of toxic side effects. The CBD has attracted much attention from scientific community due to its beneficial therapeutic potential. Researches show that the CBD has anti-inflammatory, anti-necrotic, and antioxidant properties and has significant therapeutic effects for patients with multiple sclerosis, Alzheimer's disease, epilepsy, and Parkinson's disease. There are two CBD products approved by U.S. food and drug administration (FDA) on the market, including Epidiolex® (oral solution of pure CBD) and Sativex® (oral mucosa spray of CBD and Δ-9-tetrahydrocannabinol). However, the CBD has low water-solubility, instability of absorption in the gastrointestinal system and first-pass metabolism, resulting in 6% oral bioavailability. Meanwhile, due to the extreme lipophilicity (log P: 5.79) of the CBD, the CBD is prone to reside in stratum corneum of skin, presenting a certain challenge when attempting to deliver the CBD to deeper layers of skin. Therefore, passive diffusion-based transdermal systems are difficult to achieve the circulation of the CBD in vivo.

Nanonization is defined as a pharmaceutical process that involves reducing a particle size of active pharmaceutical ingredients to a nanoscale range, which means obtaining the particle size in a submicron range, i.e., the particle size is less than 1 micrometer (μm). According to the Nois-Whitney equation, a decrease in the particle size of a drug leads to an increase in a surface area of the drug, resulting in a proportional increase in the dissolution rate and better absorption of drugs with poor solubility. In recent years, in order to improve solubility and bioavailability of the CBD, researchers develop various methods for nanosizing the CBD, such as oral self-emulsifying systems, nanoliposomes, and nanomicelles etc., however, these methods have limited solubilization of the CBD, and systems are not stable.

Microneedles are an enhancement technology of active skin penetration, and the microneedles have a needle-liked structure with a length of several hundred nanometers. The microneedles can create micron-sized holes on the skin to enhance drug delivery without irritating nerves associated with pain, and can increase patient compliance and reduce pain.

In response to the low water-solubility, low oral bioavailability, and unstable and limited solubilization of the CBD, a technology of nanosizing high dose CBD need to be developed in junction with the microneedles to improve storage stability and skin penetration of the CBD, reduce administration frequency, and improve bioavailability and patient compliance.

SUMMARY

Based on above problems, the disclosure aims at providing a nanonization method for CBD, a nanosized CBD suspension (i.e., nanonized CBD suspension) therefrom and applications thereof.

In order to achieve above purposes, the disclosure utilizes below technical solutions.

The disclosure provides the nanonization method for the CBD, including following steps.

The CBD is dissolved to a good solvent (i.e., powerful solvent or potent solvent) to obtain CBD-good solvent solution, the CBD-good solvent solution is added to aqueous solution of a stabilizer to obtain mixed solution, and the mixed solution is ultrasonicated followed by removing the good solvent by rotary evaporation from the mixed solution to obtain the nanosized CBD suspension.

The stabilizer includes one or more selected from the group consisting of poloxamer, Tween, polyoxyethylene alkyl ether, polyvinyl pyrrolidone, hydroxypropyl methyl cellulose and carboxymethyl chitosan. The nanosized CBD suspension has a high concentration of the CBD, a high drug loading efficiency and can control a particle size of the nanosized CBD in the nanosized CBD suspension.

In an embodiment, the polyoxyethylene alkyl ether includes polyoxyethylene (20) cetyl ether (BRIJ 58) or polyoxyethylene (20) oleyl ether (BRIJ 98)

In an embodiment, when the stabilizer includes more selected from the group consisting of the poloxamer, the tween, the polyoxyethylene alkyl ether, the polyvinyl pyrrolidone, the hydroxypropyl methyl cellulose and the carboxymethyl chitosan, there is no requirement for a ratio of the selected materials, and the selected materials can be mixed at any ratio. In some embodiments, the stabilizer is a mixture of the tween and the hydroxypropyl methyl cellulose at a weight ratio of 1:0.5, the stabilizer is a mixture of the tween and the polyvinyl pyrrolidone at a weight ratio of 1:0.5 to 1:0.7, the stabilizer is a mixture of the tween and the carboxymethyl chitosan at a weight ratio of 1:0.7 to 1:0.8, or the stabilizer is a mixture of the poloxamer and the polyvinyl pyrrolidone at a weight ratio of 1:0.4, etc.

In an embodiment, a weight ratio of the CBD to the stabilizer is 1:0.1-1:10. In some embodiments, the weight ratio of the CBD to the stabilizer includes but not limited to 1:0.1-1:5, 1:0.1-1:3, 1:0.1-1:2, 1:0.1-1:1.2, 1:0.1-1:0.8, 1:0.1-1:0.6, 1:0.1-1:0.5, 1:0.3-1:5, 1:0.3-1:3, 1:0.3-1:2, 1:0.3-1:1.2, 1:0.3-1:0.8, 1:0.3-1:0.6, 1:0.3-1:0.5, 1:0.5-1:5, 1:0.5-1:3, 1:0.5-1:2, 1:0.5-1:1.2, 1:0.5-1:0.8, 1:0.5-1:0.6, 1:0.3, 1:0.5, 1:0.6, 1:0.8 and 1:1.2 etc. In above condition, the nanosized CBD suspension has a high concentration of the nanosized CBD, the high drug loading efficiency and can control the particle size of the nanosized CBD in the nanosized CBD suspension.

In an embodiment, the concentration of the CBD in the CBD-good solvent solution is 20-500 milligrams per milliliter (mg/mL). In some embodiments, the concentration of the CBD in the CBD-good solvent solution includes but not limited to 25-500 mg/mL, 25-400 mg/mL, 25-300 mg/mL, 25-200 mg/mL, 25-150 mg/mL, 25-100 mg/mL, 100-500 mg/mL, 100-400 mg/mL, 100-300 mg/mL, 100-200 mg/mL, 100-150 mg/mL, 150-500 mg/mL, 150-400 mg/mL, 150-300 mg/mL, 150-200 mg/mL, 200-500 mg/mL, 200-400 mg/mL, 200-300 mg/mL, 300-500 mg/mL, 300-400 mg/mL, 25 mg/mL, 100 mg/mL, 150 mg/mL, 200 mg/mL, 300 mg/mL, 400 mg/mL and 500 mg/mL, etc.

In an embodiment, the good solvent includes one or more selected from the group consisting of ethanol ($C_2H_6O$), isopropanol ($C_3H_8O$), propylene glycol ($C_3H_8O_2$), ethyl acetate ($C_4H_8O_2$), dimethyl sulfoxide ($C_2H_6OS$), dichloroethane ($C_2H_4Cl_2$) and polyethylene glycol.

In an embodiment, the concentration of the stabilizer in the aqueous solution of the stabilizer is 10-100 mg/mL. In some embodiments, the concentration of the stabilizer in the aqueous solution of the stabilizer include but not limited to 20-50 mg/mL, 20-30 mg/mL, 30-50 mg/mL, 20 mg/mL and 30 mg/mL etc.

In an embodiment, a volume ratio of the good solvent to water is 1:1-1:10. In some embodiments, the volume ratio of the good solvent to the water includes but not limited to 1:1-1:7, 1:1-1:5, 1:1-1:3, 1:1-1:2, 1:2-1:7, 1:2-1:5, 1:2-1:3, 1:3-1:7, 1:3-1:5, 1:1, 1:2, 1:3, 1:4, 1:5, 1:7 and 1:10 etc.

In an embodiment, the mixed solution is ultrasonicated at a power of 25 to 75 watts (W) for 5 to 30 minutes (min).

In an embodiment, in the nanosized CBD suspension, a concentration of the nanosized CBD is 10 to 100 mg/mL, and the particle size of the nanosized CBD is 50 to 1000 nanometers (nm).

Furthermore, the disclosure provides the nanosized CBD suspension prepared through above method.

Furthermore, the disclosure provides a dissolving microneedle, prepared by raw materials including an excipient and a pharmaceutical ingredient containing the nanosized CBD suspension as described above.

In an embodiment, the content of the nanosized CBD in the dissolving microneedle is 1.5 to 25 weight percent (wt %).

In an embodiment, the excipient includes one or more selected from the group consisting of polyvinyl pyrrolidone, polyvinyl alcohol, sodium carboxymethyl cellulose, hyaluronic acid, and hydroxyethyl cellulose.

In an embodiment, the raw materials further include a pore-forming agent, the role of the pore-forming agent includes promoting dissolution of a needle tip.

In an embodiment, the pore-forming agent is conducive to an entry of intradermal water molecules into a matrix of the needle tip and modulate the release rate of drugs. The pore-forming agent includes but is not limited to, trehalose, maltose, sucrose and/or magnesium chloride.

In an embodiment, the dissolving microneedle is a one-piece needle or a layered needle. When the dissolving microneedle is the layered needle, the pharmaceutical ingredient containing the nanosized CBD suspension is placed in the needle tip.

In an embodiment, the dissolving microneedle is a coated microneedle.

The disclosure provides a preparation method for the dissolving microneedle, including following steps.

The pharmaceutical ingredient containing the nanosized CBD suspension is mixed with the excipient to obtain aqueous solution, the aqueous solution is placed in a microneedle mold or a microneedle tip mold and then is dried to obtain the dissolving microneedle or the needle tip of the dissolving microneedle.

In an embodiment, when the dissolving microneedle is the one-piece needle, the preparation method for the dissolving microneedle includes following steps.

The pharmaceutical ingredient containing the nanosized CBD suspension is mixed with the excipient to obtain the aqueous solution, the aqueous solution is placed in a microneedle mold and then is dried to obtain the dissolving microneedle.

When the dissolving microneedle is the layered needle, the preparation method for the dissolving microneedle includes following steps.

The pharmaceutical ingredient containing the nanosized CBD suspension is mixed with the excipient to obtain aqueous solution of the needle tip, the aqueous solution of the needle tip is placed in a microneedle mold and then is dried followed by adding substrate solution into the microneedle mold, and then the microneedle mold is vacuumed under negative pressure and dried to obtain the dissolving microneedle.

In an embodiment, in the aqueous solution, the solid content of the excipient is 10-25%, and the solid content of the pore-forming agent is 0.03-1%.

The disclosure has beneficial effects as below.

In the nanonization method for the CBD of the disclosure, the nanosized CBD suspension is obtained based on the nanonization technology that reduces the particle size of an insoluble drug, i.e., a particle size of the CBD. In the nanosized CBD suspension, the solid content of the CBD is high, and thus the nanonization method for CBD achieves solubilization of the CBD. In the preparation method for the dissolving microneedle of the disclosure, the dissolving microneedle is prepared by adding the excipient to the nanosized CBD suspension, eliminating a solid-state method for nanosizing an insoluble drug suspension in the related art and improving the stability of nanosized drugs. A drug-targeting property of the dissolving microneedle is used to achieve transdermal administration of the insoluble drug, improving the skin penetration rate of the CBD, reducing administration frequency compared to oral drugs and improving bioavailability.

BRIEF DESCRIPTION OF DRAWINGS

Specific embodiments of the disclosure are described in further detail below with accompanying drawings.

DETAILED DESCRIPTION OF EMBODIMENTS

Figure 1:
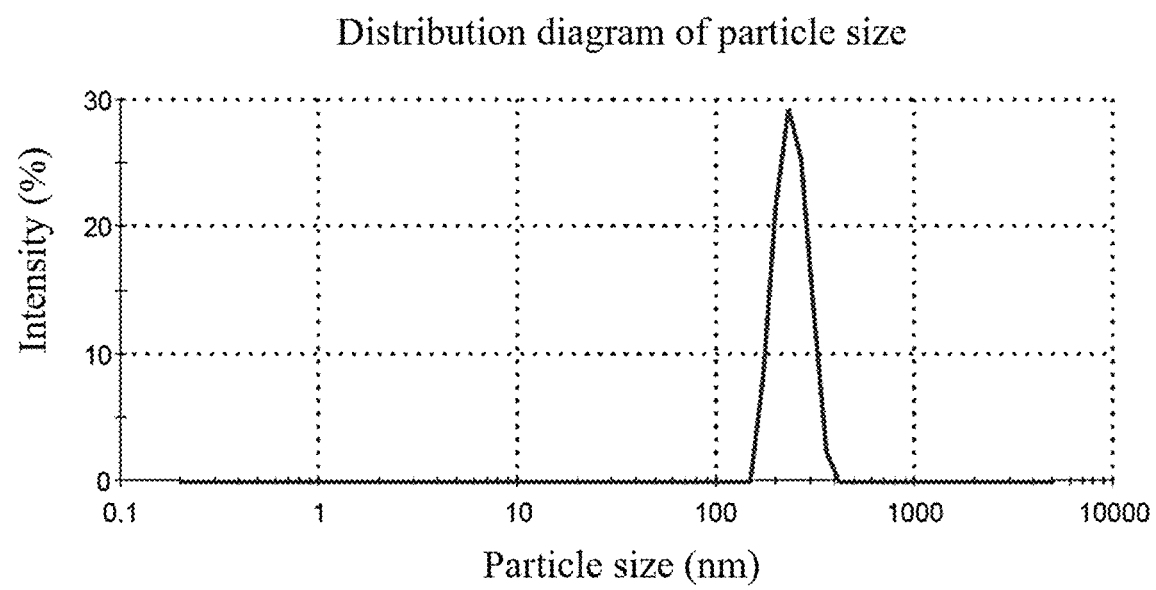
FIG. 1 illustrates a schematic distribution diagram of particle sizes of a nanosized CBD suspension prepared in embodiment 10 of the disclosure.

To describe the disclosure more clearly, the disclosure is further described below through specific embodiments with accompanying drawings. Similar components in the accompanying drawings are indicated by same reference numerals. It should be understood by those skilled in the art that detailed descriptions below are illustrative rather than restrictive and should not be used to limit protection scope of the disclosure.

Embodiment 1

Preparation and evaluation of a nanosized CBD suspension are below.

The nanosized CBD suspension is prepared through following steps.

The preparation of the nanosized CBD suspension: 0.2 gram (g) CBD is dissolved into 1 milliliter (mL) absolute ethanol as an organic phase, aqueous solution of tween at a weight concentration (i.e., weight per weight, w/w) of 2% is taken as an aqueous phase, and a volume ratio of the organic phase to the aqueous phase for mixing the organic phase and the aqueous phase is controlled to be 1:5. The organic phase is slowly added dropwise to the aqueous phase to obtain mixed solution, the mixed solution is ultrasonicated at a power of 25 W for 10 min, and then an organic solvent (i.e., the absolute ethanol) is removed by rotary evaporation from the mixed solution to obtain a nanosized tween-CBD suspension.

A content test: the nanosized tween-CBD suspension prepared in the embodiment 1 is diluted 100 times with a mobile phase (i.e., acetonitrile water solution) at a ratio of acetonitrile to water of 75:25, high performance liquid chromatography (HPLC) is used for the content test and calculation of a drug-loading rate.

The drug-loading rate=an actual concentration of the CBD/a theoretical concentration of the CBD× 100%.

The theoretical concentration of the CBD=an amount of added CBD/volume of the aqueous phase.

A measurement of a particle size: the nanosized tween-CBD suspension prepared in the embodiment 1 is diluted 100 times with ultrapure water and then is measured by a nano-particle size potential analyzer (MASTERSIZER 2000).

Compared Embodiment 1

Preparation of a nanosized CBD suspension through stirring includes the following steps.

0.2 g CBD is dissolved into 1 mL absolute ethanol as an organic phase, 2% (w/w) aqueous solution of tween is taken as an aqueous phase, and a volume ratio of the organic phase to the aqueous phase for mixing the organic phase and the aqueous phase is controlled to be 1:5. The organic phase is slowly added dropwise to the aqueous phase under magnetic stirring to obtain mixed solution, and an organic solvent is removed by rotary evaporation from the mixed solution to obtain a nanosized tween-CBD suspension.

After measurement, an actual concentration of the CBD is measured to be 17.0 mg/mL, a drug-loading rate is measured to be 42.5%, and a particle size of nanosized CBD is measured to be about 93 nm.

Compared Embodiment 2

Preparation of nanosized CBD emulsion through stirring includes the following steps.

0.2 g CBD is added to 5 mL 2% (w/w) aqueous solution of tween to obtain mixed solution, the mixed solution is magnetically stirred for 24 hours (h) to obtain the nanosized CBD emulsion.

After measurement, an actual concentration of the CBD is measured to be 10.1 mg/mL, a drug-loading rate is measured to be 25.2%, and a particle size of nanosized CBD is measured to be about 55 nm.

Embodiment 2-Embodiment 9

A preparation method is referred to the embodiment 1, parameters of each group in the embodiments 2-9 are shown in table 1.

TABLE 1

Aqueous phase is 3% (w/w) aqueous solution of tween, ultrasonication power is 45 W, ultrasonication time is 10 min

| Group | CBD concentration in good solvent | Good solvent | Volume ratio of good solvent to water | Actual concentration of CBD (mg/mL) | Drug-loading rate | Particle size of nanosized CBD (nm) |
|---|---|---|---|---|---|---|
| Embodiment 2 | 25 | polyethylene glycol | 1:1 | 18.3 | 73.2% | 476 |
| Embodiment 3 | 100 | isopropanol | 1:2 | 25.2 | 76.4% | 257 |
| Embodiment 4 | 150 | dichloroethane | 1:3 | 40.6 | 81.2% | 878 |
| Embodiment 5 | 200 | propylene glycol | 1:4 | 38.1 | 76.2% | 335 |
| Embodiment 6 | 300 | dimethyl sulfoxide | 1:5 | 41.5 | 69.2% | 176 |
| Embodiment 7 | 400 | ethanol | 1:7 | 49.8 | 87.2% | 443 |
| Embodiment 8 | 500 | ethanol | 1:5 | 91.8 | 91.8% | 109 |
| Embodiment 9 | 500 | ethyl acetate | 1:10 | 41.7 | 83.4% | 89 |

After measurement, the actual concentration of the CBD is measured to be 24.7 mg/mL, the drug-loading rate is measured to be 61.8%, and the particle size of nanosized CBD is measured to be about 284 nm.

Above results show that ultrasonic anti solvent precipitation method in the embodiments has a better solubilizing effect on CBD, compared to methods used in the compared embodiments 1-2.

Embodiment 10

Preparation of a nanosized CBD suspension includes following steps.

0.3 g CBD is dissolved into 1 mL absolute ethanol as an organic phase, 3% (w/w) aqueous solution of tween is taken as an aqueous phase, and a volume ratio of the organic phase to the aqueous phase for mixing the organic phase and the aqueous phase is controlled to be 1:5. The organic phase is slowly added dropwise to the aqueous phase to obtain mixed solution, the mixed solution is ultrasonicated at a power of 45 W for 10 min, and then an organic solvent is removed by rotary evaporation from the mixed solution to obtain the nanosized CBD suspension.

After measurement, an actual concentration of the CBD is measured to be 46.4 mg/mL, a drug-loading rate is measured to be 77.33%. As shown in FIG. 1, a particle size of nanosized CBD in the embodiment 10 is measured to be about 128 nm.

Embodiments 11-24 and Compared Embodiments 3-6

Different stabilizers are selected to prepare nanosized CBD suspensions. A preparation method is referred to the embodiment 1, with formulations shown in table 2 below.

TABLE 2

CBD concentration in absolute ethanol is 300 mg/mL, volume ratio of absolute ethanol to water is 1:5, ultrasonication power is 45 W, ultrasonication time is 10 min

| Group | Stabilizer name | stabilizer content (w/w) in aqueous phase | Actual concentration of CBD (mg/mL) | Drug-loading rate (%) | Particle size of nanosized CBD (nm) |
|---|---|---|---|---|---|
| Embodiment 11 | Tween | 1% | 18.29 | 238 | 30.48 |
| Embodiment 12 | Tween | 2% | 27.2 | 187 | 45.33 |
| Embodiment 13 | Tween | 5% | 54.1 | 89 | 90.17 |
| Embodiment 14 | Poloxamer | 2% | 31.7 | 74 | 52.83 |
| Embodiment 15 | Poloxamer | 10% | 49.6 | 52 | 82.67 |
| Embodiment 16 | polyoxyethylene (20) oleyl ether | 5% | 23.7 | 572 | 39.50 |
| Embodiment 17 | polyoxyethylene (20) cetyl ether | 10% | 35.6 | 283 | 59.33 |
| Embodiment 18 | Carboxymethyl chitosan | 2.2% | 35.5 | 708 | 59.17 |
| Embodiment 19 | Hypromellose | 3% | 42.2 | 458 | 70.33 |
| Embodiment 20 | Polyvinyl pyrrolidone | 10% | 37.8 | 536 | 63.00 |
| Embodiment 21 | Tween + Hypromellose | 2.5% + 0.5% | 43.9 | 235 | 73.17 |
| Embodiment 22 | Tween + Polyvinyl pyrrolidone | 3% + 2% | 46.1 | 245 | 76.83 |
| Embodiment 23 | Tween + Carboxymethyl chitosan | 3% + 2.2% | 47.4 | 441 | 79.00 |
| Embodiment 24 | Poloxamer + Polyvinyl pyrrolidone | 5% + 2% | 48.5 | 126 | 80.83 |
| Compared embodiment 3 | Hyaluronic acid | 3% | 3.7 | Reunion | 6.17 |
| Compared embodiment 4 | Lecithin | 5% | 1.1 | Reunion | 1.83 |
| Compared embodiment 5 | Polyvinyl alcohol | 10% | 10.3 | Reunion | 17.17 |
| Compared embodiment 6 | Cyclodextrin | 10% | 0.1 | Reunion | 0.17 |

Above results show that the stabilizers used in the compared embodiments 3-6 are not capable of preparing the nanosized CBD suspensions well enough to provide ideal solubilizing and stabilizing effects. Contrarily, the stabilizers used to prepare the nanosized CBD suspensions in the embodiments 12-24 make particle sizes of the nanosized CBD in a range of 50-1000 nm and the actual concentration of the CBD in a range of 10-60 mg/mL.

Embodiment 25-29

Referring to the embodiment 10, different ultrasonication powers and times are used for preparing nanosized CBD suspensions with formulations shown in table 3 below.

TABLE 3

| Group | Formulation | Ultrasonication power and time | Actual concentration of CBD (mg/mL) | Drug-loading rate (%) | Particle size of nanosized CBD (nm) |
|---|---|---|---|---|---|
| Embodiment 25 | CBD concentration in absolute ethanol is 300 mg/mL, | 45 W, 5 min | 34.5 | 57.50 | 111 |
| Embodiment 26 | | 45 W, 20 min | 42.0 | 70.00 | 109 |

TABLE 3-continued

| Group | Formulation | Ultra-sonication power and time | Actual concentration of CBD (mg/mL) | Drug-loading rate (%) | Particle size of nanosized CBD (nm) |
|---|---|---|---|---|---|
| Embodiment 27 | volume ratio of absolute ethanol to water is 1:5, stabilizer is 3% (w/w) tween | 45 W, 30 min | 37.8 | 63.00 | 148 |
| Embodiment 28 | | 25 W, 10 min | 28.5 | 47.50 | 160 |
| Embodiment 29 | | 70 W, 10 min | 48.4 | 80.67 | 109 |

Above results show that in the embodiments 26-29, when the ultrasonication power is in a range of 25-75 W and the ultrasonication time is in a range of 5-30 min, requirements of target concentrations and nanonization can be met.

Embodiment 30

Figure 2:
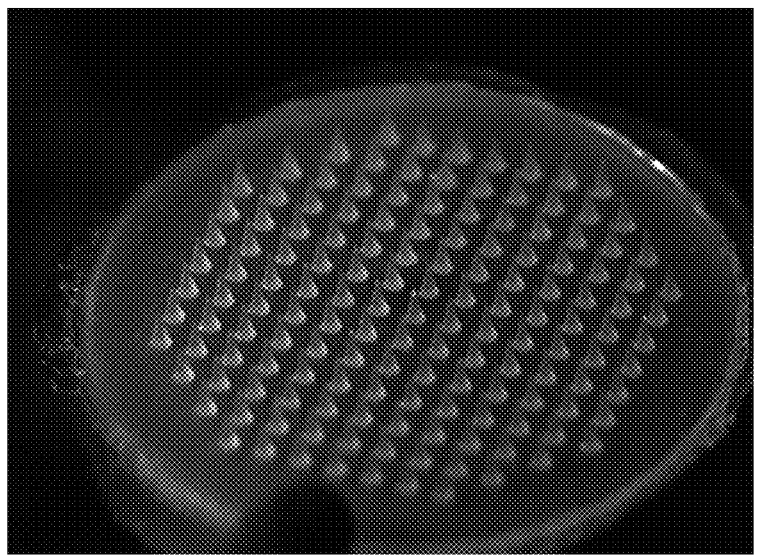
FIG. 2 illustrates an optical micrograph of a dissolving microneedle prepared in embodiment 30 of the disclosure.

A preparation method for a one-piece microneedle containing nanosized CBD includes following steps:
(1) Preparation of microneedle solution: 4.0 g nanosized CBD suspension prepared in the embodiment 10 is added to an excipient, i.e., 1.0 g polyvinyl pyrrolidone, and then mixed well to obtain mixed solution, air bubbles are removed by centrifuging the mixed solution to obtain the microneedle solution.
(2) Preparation of the one-piece microneedle: 60 microliter (μL) microneedle solution is added into a polydimethylsiloxane (PDMS) mold and then is vacuumed for 5 min followed by being dried at room temperature to obtain the one-piece microneedle.
(3) Check parameters of the one-piece microneedle Microneedle completeness: A stereo microscope is used to observe the shape of the one-piece microneedle entirely, whether the one-piece microneedle is able to be completely demolded and whether a tip shape of the one-piece microneedle is intact. Topography of the one-piece microneedle in the embodiment 30 under an optical microscope is shown in FIG. 2. The microneedle array includes 144 (i.e., 12×512) conical arrays with an area of 0.56 square centimeter ($cm^2$) and a needle height of 500 μm.

Figure 3:
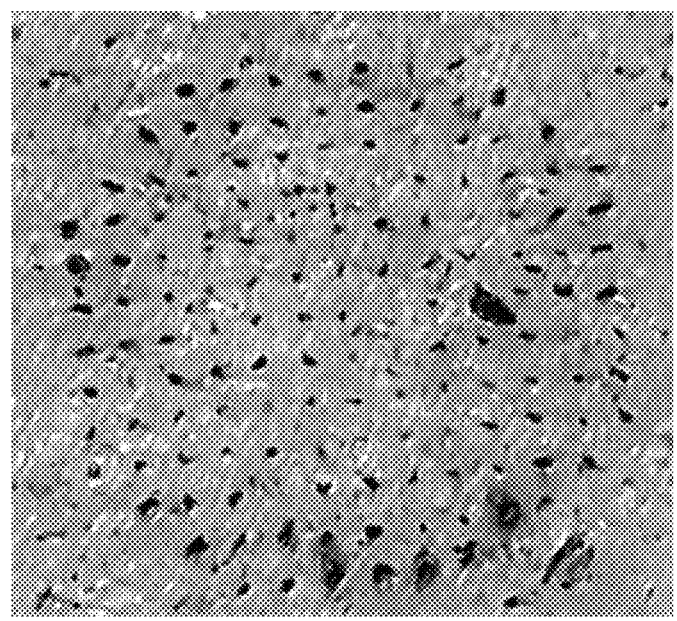
FIG. 3 illustrates a schematic diagram of a piece of ex vivo pig skin stained with trypan blue after being punctured by the dissolving microneedle prepared in embodiment 30 of the disclosure.

Microneedle penetrability: skin of a piglet ear is used and an appropriate area of the skin of the piglet ear is cut to be tested. A tip of the one-piece microneedle is pressed flat downward to puncture the skin with needle insertion pressure of 20 newton (N) applied on the back of the microneedle for 10 min, and then the one-piece microneedle is removed from the skin, trypan blue solution is added dropwise to a punctured part of the skin to obtain stained skin, and after 5 min for staining, the stained skin is wiped down, and then observed. When neatly colored pinhole arrays are observed on the stained skin, the one-piece microneedle has penetrability. A puncture result of the embodiment 30 is shown in FIG. 3, pinholes are clear with the naked eye, and pinhole arrays on the stained skin are neat and complete.

Embodiments 31-34 and Compared Embodiments 7-11

One-piece dissolving microneedles prepared by different excipients that inventors tried are listed in the embodiments 31-34 and the compared embodiments 7-11. Excipients in the compared embodiments 7-11 include poly-γ-glutamic acid (γ-PGA), chondroitin sulfate (CS), dextran (DEX), hydroxypropyl methyl cellulose (HPMC) and hydroxypropyl cellulose (HHPC). Excipients in the embodiments 31-34 include polyvinyl alcohol (PVA), hyaluronic acid (HA), hydroxyethyl cellulose (HEC), and sodium carboxymethyl cellulose (CMC). All microneedles in the embodiments 31-34 and compared embodiments 7-11 are prepared through the same preparation method as that of the embodiment 30 according to weight percentages of excipients given in table 1.

According to a testing method same as that of the embodiment 30, penetrability and completeness and needle color of the microneedles are tested, and results are shown in table 4.

TABLE 4

| Group | Excipient | Weight content percentage of excipient | Completeness | Penetrability | Color |
|---|---|---|---|---|---|
| Embodiment 31 | PVA | 20% | Complete | Yes | Clear |
| Embodiment 32 | CMC | 10% | Complete | Yes | Clear |
| Embodiment 33 | HA | 20% | Complete | Yes | Clear |
| Embodiment 34 | HEC | 20% | Complete | Yes | Clear |
| Compared embodiment 7 | γ-PGA | 10% | Complete | No | Pale yellow |
| Compared embodiment 8 | CS | 10% | Complete | Yes | Yellow |
| Compared embodiment 9 | DEX | 10% | Incomplete | Yes | Clear |
| Compared embodiment 10 | HPMC | 20% | Curly | Yes | Yellow |
| Compared embodiment 11 | HHPC | 30% | Complete | No | Clear |

As can be seen from table 4, different excipients are used in the compared embodiment 7-11, microneedles become yellow during preparation when the γ-PGA, the CS or the HPMC is used, not meet appearance requirements of microneedles. A microneedle prepared with the DEX is brittle and a tip of the microneedle prepared with the DEX is prone to breakage during demolding, not meeting the appearance requirements of microneedles. A microneedle prepared with the HHPC does not have penetrability, not meet using requirements of microneedles. Appearance and penetrability of microneedles prepared with the PVA, PVP, CMC, HA or HEC can meet the appearance and use requirements of microneedles.

Embodiments 35-36 and Compared Embodiment 12

A Proportion Range of CBD in a Dissolving Microneedle.

A concentration range of nanosized CBD prepared is 10-100 mg/mL and upper and lower limits of a drug-loading rate of a dissolving microneedle should be set. Therefore, a CBD concentration of 10 mg/mL is selected to examine a lower limit of the drug-loading rate, and a CBD concentration of 100 mg/mL is selected to examine an upper limit of the drug-loading rate.

The dissolving microneedle is prepared through a preparation method in the embodiment 30 and with a weight percentage of an excipient given in table 5, and needle formation and the drug loading rate of the dissolving microneedle are examined.

Microneedle content test: A sample of the dissolving microneedle is added into a centrifuge tube, and then 3 mL mobile phase (i.e., acetonitrile:water=75:25) is added into the centrifuge tube, and then the centrifuge tube is oscillated on a vortex for 120 min to obtain the CBD in groups, the CBD is filtered through a 0.22 μm filter membrane to a liquid phase vial and then tested by HPLC.

A proportion of the CBD in the dissolving microneedle=CBD content/total solid content in the dissolving microneedle×100%.

TABLE 5

| Group | CBD concentration in a nanosized CBD suspension (mg/mL) | Weight percentage of excipient | Drug-loading rate of dissolving microneedle |
|---|---|---|---|
| Embodiment 35 | 10 | 40% HA-30% PVP 30% PVA | 1.5% |
| Embodiment 36 | 100 | 30% PVA | 25% |
| Compared embodiment 12 | 100 | 20% PVA | 33.3% |

The drug-loading rate of the dissolving microneedle is related to an amount of added CBD and the weight percentage of the excipient. If the lower limit of the drug-loading rate is to be discussed, the weight percentage of the excipient should be improved as high as possible. An excipient at 70% weight percentage is selected in the embodiment 35, a dissolving microneedle prepared in the embodiment 35 has good needle formation with 1.5% drug-loading rate. If the weight percentage of the excipient is higher, the drug-loading rate should be lower. A dissolving microneedle prepared in the embodiment 36 has a complete needle tip and good toughness. However, when the weight percentage of the PVA is reduced, a dissolving microneedle prepared in the compared embodiment 12 has poor toughness, and a needle tip in the compared embodiment 12 may be broken. Therefore, a range of the drug-loading rate should be controlled within 25%.

Embodiments 37-42 and Compared Embodiment 13

Different pore-forming agents are used to prepare a one-piece microneedle containing nanosized CBD.
(1) Preparation of microneedle solution: 5.0 g nanosized CBD suspension prepared in the embodiment 10 is added with an excipient, i.e., 0.70 g HA and 0.30 g PVP, and then added with a pore-forming agent according to table 6 to obtain mixed solution, the mixed solution is mixed well and then is centrifuged to remove air bubbles to obtain the microneedle solution.
(2) Preparation of a one-piece microneedle: 60 μL microneedle solution is added into a PDMS mold and then is vacuumed for 5 min followed by being dried at room temperature to obtain the one-piece microneedle.
(3) A microneedle solubility experiment: the one-piece microneedle is attached to a piece of ex vivo pig skin for 30 seconds(s), a pressure-sensitive adhesive is attached to a substrate layer for a period of time. The remained part of the one-piece microneedle is placed under a fluorescence microscope to find height changes of the one-piece microneedle for transdermal solubility of the one-piece microneedle.

Figure 4:
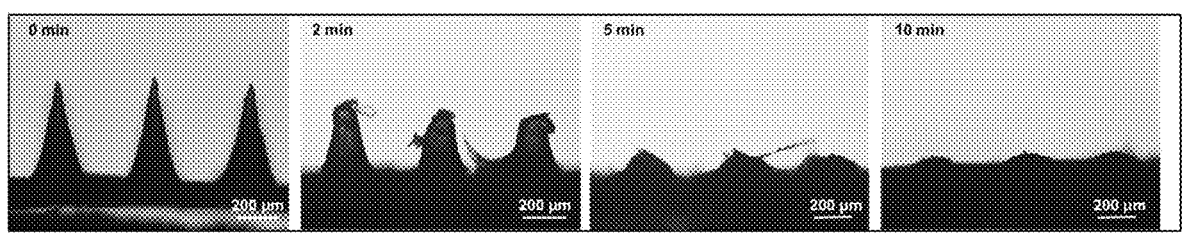
FIG. 4 illustrates a schematic diagram of dissolved height change of a dissolving microneedle prepared in an embodiment 39 of the disclosure after puncturing a piece of ex vivo pig skin.

Results of the microneedle solubility experiment in the embodiment 39 are shown in FIG. 4. It can be seen that a one-piece microneedle prepared in the embodiment 39 is dissolved very fast, and a needle tip of the one-piece microneedle prepared in the embodiment 39 is dissolved completely in 10 min. It is indicated that the one-piece microneedle can enter skin and release drugs very quickly.

TABLE 6

| | CBD concentration in nanosized CBD suspension is 45 mg/mL, excipient is 11.6 wt % HA + 5 wt % PVP | | Needle tip dissolved rate in 5 min |
|---|---|---|---|
| Group | Pore-forming agent name | Weight percentage of pore-forming agent | |
| Embodiment 37 | Magnesium chloride | 0.03% | 70% |
| Embodiment 38 | Magnesium chloride | 0.1% | 76% |
| Embodiment 39 | Trehalose | 0.25% | 74% |
| Embodiment 40 | Trehalose | 1% | 82% |
| Embodiment 41 | Maltose | 0.5% | 79% |
| Embodiment 42 | Sucrose | 0.25% | 75% |
| Compared embodiment 13 | / | / | 65% |

Above results indicate that a dissolved speed of the one-piece microneedle is improved after the pore-forming agent is added, and the pore-forming agent is conducive to releasing drugs.

Embodiment 43

An Accelerated Stability Test of a Microneedle Containing CBD:

A patch of a microneedle prepared in the embodiment 39 is packed in a blister and an aluminum-plastic bag and then placed at 50° C. for 3 months. CBD content in the microneedle prepared in the embodiment 39 is tested by HPLC at day $0^{th}$ and a third month. According to a test by HPLC, the CBD content in the microneedle can remain at 99.3%, indicating that after the CBD is prepared into the microneedle, drug stability can be kept well and a microneedle dosage form is easy to save and transport.

Embodiment 44

Determination of In Vitro Drug Release from a Microneedle Containing CBD.

A microneedle prepared in an embodiment is placed in a dialysis bag and then disperse with 200 μL receiving solution to obtain a sample, the dialysis bag containing the sample is sealed and then suspended in a stoppered conical flask containing 5 mL receiving solution. The receiving solution is 1% tween 80-phosphate-buffered saline (PBS). The stoppered conical flask with the dialysis bag suspended is filled with magnetic particles, with a magnetic stirring speed of 280 revolutions per minute (rpm), and placed in a water bath at a constant temperature of 37±0.2 degrees Celsius (° C.). The sample in the stoppered conical flask is taken out at regular times to obtain removal solution, and release medium with same volume as the sample is added into the stoppered conical flask simultaneously. The removal solution is filtered through a 0.45 μm filter membrane, and then is transferred to a liquid phase vial and then is tested by HPLC to determine CBD concentration in the sample.

Figure 5:
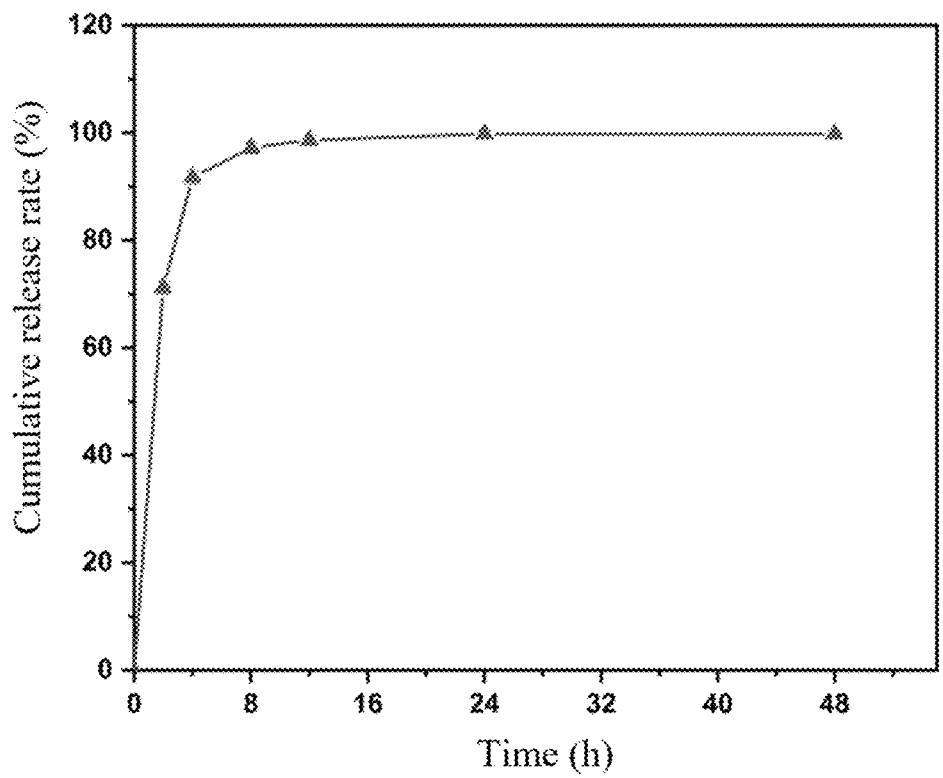
FIG. 5 illustrates a schematic in vitro drug release curve diagram of the dissolving microneedle prepared in embodiment 39 of the disclosure.

FIG. 5 illustrates an in vitro drug release curve of a microneedle prepared in the embodiment 39. It can be seen that the microneedle prepared in the embodiment 39 has a sudden release phenomenon in the first 2 h, and a release rate can be reached to 1.25±1.19%. After 8 hours, the in vitro drug release curve tends to be smooth, and drug release is finally complete.

Embodiment 45

An In Vivo Dermal Dynamics Experiment of a CBD Microneedle in Rats

Male adult Sprague-Dawley (SD) rats weighing about 250 g are fixed, hair is removed from abdominal skin of each male adult SD rat by hair removal cream, and then a microneedle punctures the abdominal skin of each male adult SD rat, after kept puncturing for 2, 4, 8, 12, and 24 h separately, the microneedle is removed. Then the abdominal skin is cleaned twice with a cotton ball moistened with medical alcohol to obtain a skin sample. The skin sample is preserved in a 5 mL centrifuge tube with the removed microneedle to extract remained microneedle content, and a content analysis is performed by HPLC.

Figure 6:
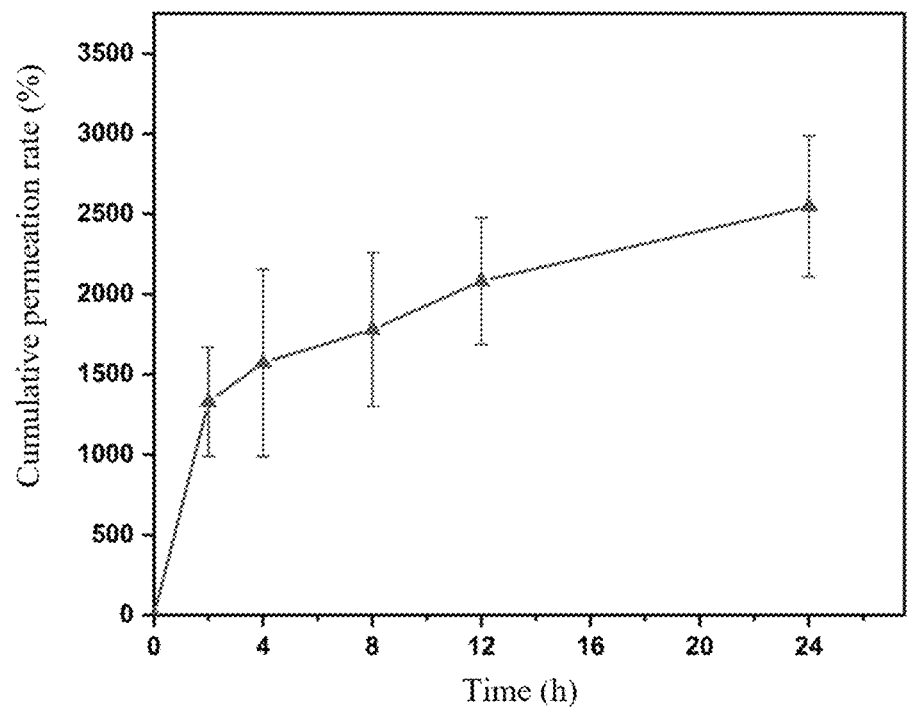
FIG. 6 illustrates a schematic cumulative permeation curve diagram of the dissolving microneedle prepared in embodiment 39 of the disclosure.

FIG. 6 illustrates a cumulative permeation curve diagram of a microneedle prepared in the embodiment 39 after the in vivo dermal dynamics experiment. It can be seen that, in the first 2 h, the permeation speed of the microneedle prepared in the embodiment 39 can be 1246.90±404.07 micrograms per square centimeter ($\mu g/cm^2$), and after the first 2 h, the permeation speed slows down.

Embodiment 46

An In Vivo Pharmacokinetics Experiment of a CBD Microneedle in a Rat

A male adult SD rat weighing about 250 g is fixed, hair is removed from abdominal skin of the male adult SD rat by hair removal cream, and then a microneedle punctures vertically the abdominal skin of the male adult SD rat for a 24 h administration, and then the microneedle is removed. Blood is collected from a tail vein of the male adult SD rat at predetermined time points before and after the 24 h administration, the blood is placed into a heparinized tube and then centrifuged at 4° C. and 5000 rpm for 10 min to collect plasma at an upper layer. The plasma is preserved at 80° C., and then the content test is performed.

Figure 7:
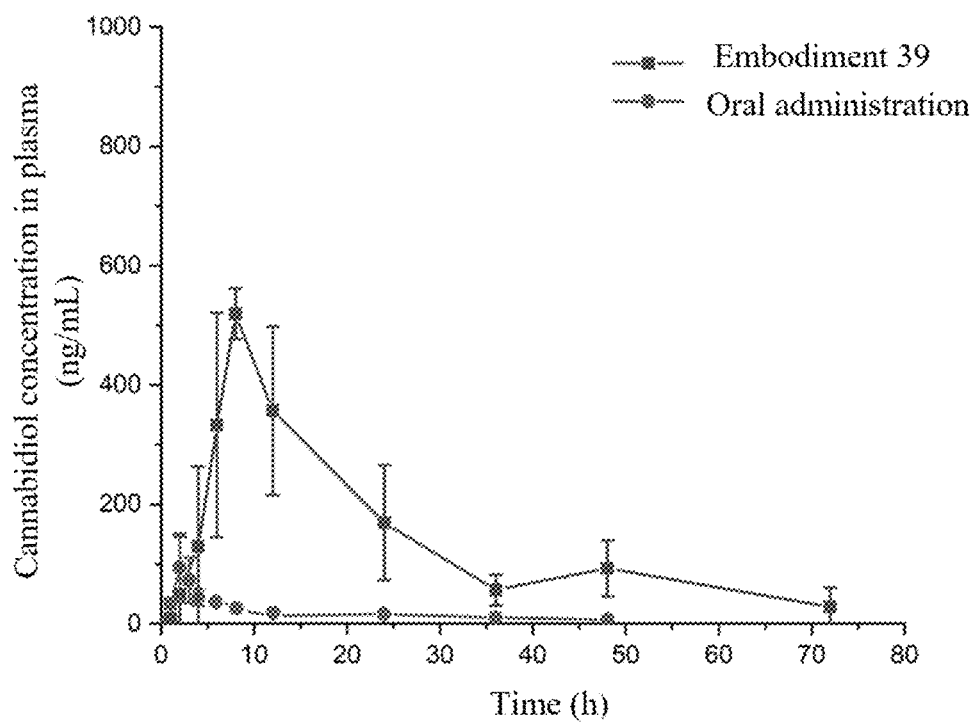
FIG. 7 illustrates a pharmacokinetic curve diagram of the dissolving microneedle prepared in embodiment 39 of the disclosure in rats.

FIG. 7 illustrates a result of the in vivo pharmacokinetics experiment of a microneedle prepared in the embodiment 39. It can be seen that a microneedle administration can maintain drug concentration in plasma for 3 days, while a gavage group (i.e., oral administration) can only maintain the drug concentration in plasma for 2 days, and area under a curve of the microneedle administration is 12 times as large as area under a curve of the oral administration. It is indicated that CBD microneedle formation of the disclosure not only improve bioavailability of the CBD but also achieves a certain delayed-release effect, reduce administration frequency and improves patient compliance.

Compared Embodiment 14

Preparation, Heat Resistance Evaluation, and In Vitro Release Evaluation of a One-Piece Microneedle Prepared Through an Organic Solvent Dissolving CBD.

N,N-dimethylacetamide (DMA) is used as a solvent to prepare matrix solution containing 10% (w/w) Poly Lactic-co-Glycolic Acid (PLGA), 10% (w/w) PVP and 4% (w/w) CBD. The matrix solution is mixed well to obtain microneedle solution. 50 µL microneedle solution is placed into a PDMS mold and then vacuumed for 5 min, and then heated at 50° C. for 3 h to obtain a microneedle.

The heat resistance evaluation: The microneedle prepared in the compared embodiment 14 is placed in an incubator at 60° C. for 10 days after sealed, and then the microneedle is removed and observed under an optical microscope for a side view of the microneedle to observe completeness and color of the microneedle.

Operation of the in vitro release evaluation is same as determination of in vitro drug release in the embodiment 44.

Compared Embodiments 15-18

A microneedle is prepared according to a preparation method in the compared embodiment 14. Polylactic acid (PLA), PVA, PVP and HPMC is used for compounding, DMA, N,N-dimethylformamide (DMF), and N-methyl pyrrolidone (NMP) are used as an organic solvent for dissolving. Heating and natural drying are used as a heating process for in vitro release evaluation. Results of the in vitro release evaluation in the compared embodiments 15-18 are shown in table 7.

TABLE 7

| Group | Compared embodiment 14 | Compared embodiment 15 | Compared embodiment 16 | Compared embodiment 17 | Compared embodiment 18 |
| --- | --- | --- | --- | --- | --- |
| Microneedle solution | 10% PLGA + 10% PVA + 4% CBD | 10% PLA + 10% PVP + 4% CBD | 10% PLGA + 10% HPMC + 4% CBD | 10% PVA + 10% PVP + 4% CBD | 10% PVA + 10% PVP + 4% CBD |
| Organic solvent | DMA | DMA | DMF | NMP | NMP |
| Heating process | 50° C., 3 h | 50° C., 2 h | 50° C., 1 h | 50° C., 3 h | Natural drying |
| Heat resistance | Needle tip is complete and discolored | Needle tip is complete and discolored | Needle tip is complete and discolored | Needle tip is complete and discolored | Needle tip is complete and discolored |
| in vitro release rate in 24 h | 16.7% | 25.5% | 21.8% | 23.6% | 26.3% |

When using the PLGA, PLA, PVA, PVP and HPMC, a one-piece microneedle system prepared with an organic solvent dissolving the CBD, suffers from difficulties in in vitro release and discoloration under high temperature conditions, it is indicated that dissolving the CBD with an organic solvent directly for preparing a one-piece microneedle is not suitable.

Embodiment 47

A Layered Microneedle of Nanosized CBD

The layered microneedle of nanosized CBD is prepared by following steps.

(1) Preparation of matrix solution of the layered microneedle.

Preparation of needle tip solution: 1.0 g nanosized CBD suspension prepared in the embodiment 10 containing fluorescent substance coumarin 6, is added with 0.14 g HA, 0.06 g PVP and 0.01 g trehalose in turn and then mixed well followed by being centrifuged to obtain the needle tip solution.

Preparation of substrate solution: 10.0 g ultrapure water is added into a centrifuge tube, and then the centrifuge tube is added with 10.0 g PVA to obtain a mixture, the mixture is heated and dissolved in an oven at 80° C., and then is stirred every 30 min till completely dissolution to obtain mixed solution, air bubbles are removed by centrifuging the mixed solution to obtain the substrate solution with 50% PVA solid content.

(2) Preparation of microneedle: 5 μL needle tip solution is added to a PDMS mold by a liquid dispenser and then vacuumed for 5 min, followed by naturally drying needle tip of the PDMS mold at room temperature for 30 min, and then 50 μL substrate solution are added into the PDMS mold, and then the PDMS mold is vacuumed under negative pressure for 10 min to obtain a vacuumed mold, the vacuumed mold is naturally dried and then demolded to obtain the layered microneedle.

Figure 8:
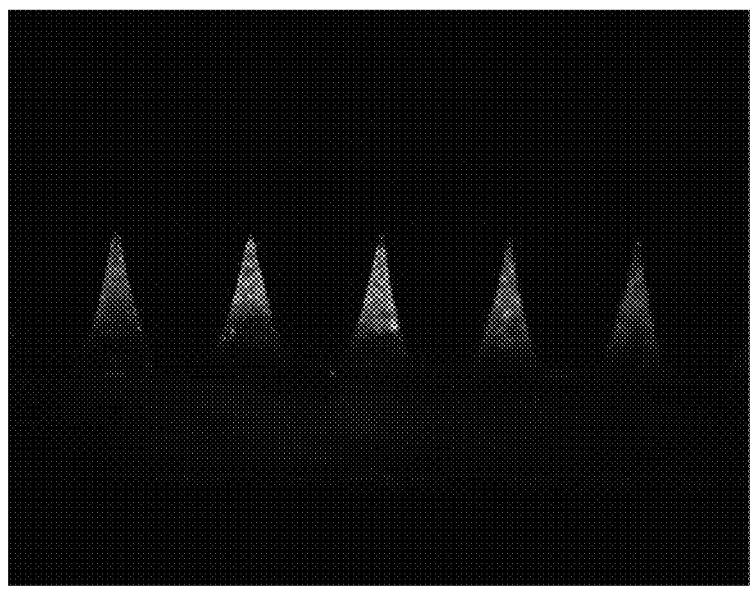
FIG. 8 illustrates a fluorescence microscope topography of a layered microneedle prepared in embodiment 47 of the disclosure.

(3) Observation of the layered microneedle: It can be observed under a fluorescence microscope that a height of the needle tip of the layered microneedle is about 300 μm as shown in FIG. 8.

(4) A microneedle solubility experiment: According to steps in the embodiment 37, it can be observed under a microscope that the needle tip with drug loaded of the layered microneedle can be dissolved completely in 5 min.

(5) Determination of in vitro drug release: the determination of in vitro drug release is performed according to steps in the embodiment 44. A cumulative release rate of the layered microneedle can be greater than 50% within a first 30 min.

Embodiment 48

A Coated Microneedle Containing Nanosized CBD

The coated microneedle is prepared by following steps.

(1) An appropriate amount of PLGA is placed in a one-piece matrix mold, and then a bottom of the one-piece matrix mold is vacuumed to obtain a vacuumed mold, the vacuumed mold is heated at 190° C. for 5 min to obtain a heated mold, polymer material is pressed flat in the heated mold and then the heated mold is cooled and demolded to obtain a polylactic acid one-piece microneedle base.

(2) Drug solution: 1.0 g nanosized CBD suspension in the embodiment 10 is added with 0.1 g PVP, 0.1 g 50% (w/w) PVA solution and 0.02 g trehalose in turn and then mixed well followed by centrifuge to obtain the drug solution.

(3) The drug solution is placed in a drug-loading pool with a height of 300 μm. The polylactic acid one-piece microneedle base is dropped with a needle tip of the polylactic acid one-piece microneedle base downward into the drug-loading pool for drug dipping to obtain a dipped microneedle base, the dipped microneedle base is left for 3 min for coating drying, a process of the drug dipping and the coating drying is repeated 4 times to obtain the coated microneedle.

(4) A microneedle solubility experiment: According to steps in the embodiment 37, it can be observed under a microscope that a needle tip with drug loaded of the coated microneedle can be dissolved completely in 30 min.

(5) Determination of in vitro drug release: the determination of in vitro drug release is performed according to steps in the embodiment 44. A cumulative release rate of the coated microneedle can be greater than 50% within the first 8 h.

It is apparent that above embodiments are only intended to illustrate the disclosure and are not intended to limit implementation of the disclosure. For those skilled in the art, limitations can also be made on the embodiments based on the above explanation and it is impossible to exhaustively list all embodiments. Any obvious amendments or modifications derived from the technical solutions of the disclosure are still within the spirit and scope of the disclosure.

What is claimed is:

1. A dissolving microneedle, comprising: an excipient and a pharmaceutical ingredient containing a nanosized cannabidiol (CBD) suspension; wherein the dissolving microneedle further comprises a pore-forming agent comprising one or more selected from the group consisting of trehalose, maltose, sucrose and magnesium chloride; and the nanosized CBD suspension comprises: nanosized CBD and a stabilizer, a concentration of the nanosized CBD in the nanosized CBD suspension is in a range of 10 to 100 mg/mL, a particle size of the nanosized CBD is in a range of 50 to 1000 nanometers (nm), and content of the nanosized CBD in the dissolving microneedle is in a range of 1.5 to 25 weight percent (wt %);

wherein the stabilizer comprises one or more selected from the group consisting of poloxamer, polysorbate, polyoxyethylene alkyl ether, polyvinyl pyrrolidone, hydroxypropyl methyl cellulose and carboxymethyl chitosan, and the excipient comprises polyvinyl pyrrolidone, polyvinyl alcohol, sodium carboxymethyl cellulose, hyaluronic acid, or hydroxyethyl cellulose.

2. A preparation method for the dissolving microneedle as claimed in claim 1, comprising following steps:

dissolving CBD to a solvent to obtain CBD-solvent solution, wherein a concentration of the CBD in the CBD-solvent solution is in a range of 20 to 500 milligrams per milliliter (mg/mL);

adding the CBD-solvent solution to aqueous solution of the stabilizer to obtain first mixed solution, ultrasonicating the first mixed solution, and then removing the solvent by rotary evaporation from the first mixed solution to obtain the nanosized CBD suspension, wherein the first mixed solution is ultrasonicated at a power of 25 to 75 watt for 5 to 30 minutes, a weight ratio of the CBD to the stabilizer is 1:0.3 to 1:5, and a concentration of the stabilizer in the aqueous solution of the stabilizer is in a range of 10 to 100 mg/ml;

mixing the excipient with the pharmaceutical ingredient containing the nanosized CBD suspension, followed by adding the pore-forming agent, to obtain second mixed solution, and centrifuging the second mixed solution to remove air bubbles to obtain aqueous solution; and placing the aqueous solution to a microneedle mold or a microneedle tip mold and then drying the aqueous solution to obtain the dissolving microneedle or a needle tip of the dissolving microneedle.

3. The dissolving microneedle as claimed in claim 1, wherein the dissolving microneedle is a layered needle, and the pharmaceutical ingredient containing the nanosized CBD suspension is disposed in a needle tip of the layered needle.

4. The dissolving microneedle as claimed in claim 1, wherein the stabilizer is a mixture of the polysorbate and the hydroxypropyl methyl cellulose at a weight ratio of 1:0.5, a mixture of the polysorbate and the polyvinyl pyrrolidone at a weight ratio of 1:0.5 to 1:0.7, a mixture of the polysorbate and the carboxymethyl chitosan at a weight ratio of 1:0.7 to 1:0.8, or a mixture of the poloxamer and the polyvinyl pyrrolidone at a weight ratio of 1:0.4.

5. The preparation method as claimed in claim 2, wherein the stabilizer is a mixture of the polysorbate and the hydroxypropyl methyl cellulose at a weight ratio of 1:0.5, a mixture of the polysorbate and the polyvinyl pyrrolidone at a weight ratio of 1:0.5 to 1:0.7, a mixture of the polysorbate and the carboxymethyl chitosan at a weight ratio of 1:0.7 to 1:0.8, or a mixture of the poloxamer and the polyvinyl pyrrolidone at a weight ratio of 1:0.4.

\* \* \* \* \*